(12) United States Patent
Gheng et al.

(10) Patent No.: US 6,561,980 B1
(45) Date of Patent: May 13, 2003

(54) AUTOMATIC SEGMENTATION OF PROSTATE, RECTUM AND URETHRA IN ULTRASOUND IMAGING

(75) Inventors: Gang Gheng, Rochester, NY (US); Haisong Liu, Rochester, NY (US); Yan Yu, Rochester, NY (US)

(73) Assignee: Alpha Intervention Technology, Inc, Rochester, NY (US)

( * ) Notice: Subject to any disclaimer, the term of this patent is extended or adjusted under 35 U.S.C. 154(b) by 40 days.

(21) Appl. No.: 09/621,867

(22) Filed: Jul. 21, 2000

Related U.S. Application Data

(60) Provisional application No. 60/206,270, filed on May 23, 2000.

(51) Int. Cl.$^7$ .................................. A61B 8/00
(52) U.S. Cl. ......................................... 600/443
(58) Field of Search .................... 600/427, 437, 600/439, 443, 461–463, 470; 606/15, 20–21, 39–41, 159, 169; 601/2, 3; 382/6

(56) References Cited

U.S. PATENT DOCUMENTS

| | | | |
|---|---|---|---|
| 4,005,699 A | | 2/1977 | Bucalo |
| 4,702,288 A | | 10/1987 | Russell, Jr. et al. |
| 5,061,266 A | * | 10/1991 | Hakky ........................ 606/15 |
| 5,373,844 A | | 12/1994 | Smith et al. |
| 5,391,139 A | | 2/1995 | Edmundson |
| 5,474,071 A | | 12/1995 | Chapelon et al. ...... 128/660.03 |
| 5,740,802 A | | 4/1998 | Nafis et al. |
| 5,748,767 A | | 5/1998 | Raab |
| 5,752,962 A | | 5/1998 | D'Urso |
| 5,797,849 A | | 8/1998 | Vesely et al. |
| 5,810,007 A | | 9/1998 | Holupka et al. |
| 5,820,559 A | * | 10/1998 | Ng et al. .................... 600/439 |
| 5,823,993 A | | 10/1998 | Lemelson |
| 5,843,016 A | | 12/1998 | Lugnani et al. |
| 5,868,757 A | | 2/1999 | Koutrouvelis |
| 5,938,583 A | | 8/1999 | Grimm |
| 6,027,446 A | * | 2/2000 | Pathak et al. ............... 600/439 |
| 6,045,508 A | | 4/2000 | Hossack et al. ............ 600/447 |
| 6,083,167 A | * | 7/2000 | Fox et al. ................... 600/439 |
| 6,095,975 A | | 8/2000 | Silvern |
| 6,129,670 A | * | 10/2000 | Burdette et al. ............ 600/427 |
| 6,200,255 B1 | | 3/2001 | Yu |
| 6,210,315 B1 | * | 4/2001 | Andrews et al. ............... 600/3 |
| 6,217,518 B1 | * | 4/2001 | Holdaway et al. .......... 600/439 |
| 6,256,529 B1 | * | 7/2001 | Holupka et al. ............ 600/427 |

* cited by examiner

*Primary Examiner*—Ali M. Imam
(74) *Attorney, Agent, or Firm*—Blank Rome Comisky & McCauley LLP

(57) ABSTRACT

An ultrasound image of a transverse cross-sectional outline of the prostate gland is acquired. For three-dimensional imaging, a series of images can be taken, one of each slice of the prostate. The initial ultrasound images are pre-processed to remove the noise and increase the contrast. The rectum edge is located from the bottom of the images. The key points on the prostate boundaries are located and connected under the iterative training of a knowledge-based model until the shape of the boundary reaches a stable state. The urethra is segmented near the center of the prostate.

48 Claims, 9 Drawing Sheets

US 6,561,980 B1

AUTOMATIC SEGMENTATION OF PROSTATE, RECTUM AND URETHRA IN ULTRASOUND IMAGING

REFERENCE TO RELATED APPLICATION

This application claims the benefit of U.S. Provisional Application No. 60/206,270, filed May 23, 2000, whose disclosure is hereby incorporated by reference in its entirety into the present disclosure.

STATEMENT OF GOVERNMENT INTEREST

The present invention was made with government support through Grant No. R44 CA78115 from the National Cancer Institute, National Institutes of Health. The government has certain rights in the invention.

FIELD OF THE INVENTION

The present invention relates generally to prostate brachytherapy (radioactive seed implantation), and more particularly concerns a method and system for determining prostate boundaries in transrectal ultrasound images.

BACKGROUND OF THE INVENTION

Prostate adenocarcinoma is the most frequently diagnosed cancer in men and remains the second leading cause of death of American men. The reported incidence of prostate cancer has been increasing in the past ten years due to increased life expectancy, prostate specific antigen (PSA) screening, and improved diagnostic techniques, including transrectal ultrasound (TRUS), CT and MRI. Autopsies of individuals dying of other causes show prostate cancer cells in 30% of men at age 50; by the age of 80 years, the prevalence is 60%. Further, prostate cancer can take up to 10 years to kill the patient after initial diagnosis. Prostate cancer is newly diagnosed in over 100,000 men in the US each year, and over 40,000 will die of the disease. These trends are expected to continue in the near future.

There are four standard treatment regimens for prostate cancer: (1) watchful waiting, (2) radical prostatectomy, (3) external beam radiation; and (4) interstitial brachytherapy. The rising incidence of earlier stage prostate disease in younger patients with longer life expectancies has brought both treatment effectiveness and the quality of life into focus. As an effective treatment option, the rapid development of transperineal prostate brachytherapy has provided an alternative for patients seeking to preserve their prostate function as well as control the cancer. Interstitial brachytherapy, which can be performed as a single outpatient treatment, is recommended for patients with early stage cancer. With a high likelihood of disease located outside the prostate, the doctors often follow external beam radiation treatments with interstitial brachytherapy. Because prostate brachytherapy is associated with a lower incidence of incontinence, impotence and rectal injury, it is emerging as a medically successful, cost-effective outpatient treatment in treating localized prostate cancer.

The interstitial brachytherapy technique is well known and is described in detail in many publications. Interstitial brachytherapy involves the accurate placement of radioactive seeds into the prostate gland according to a predetermined dosimetry plan, which is optimized to cover the whole prostate with enough dosimetry. The implant needles, guided by a grid template, are inserted into the prostate gland under the guidance of a transrectal ultrasound probe, which is inserted into the rectum of the patient. Then a seed applicator or spacer is used to locate the seeds at special positions.

For calculating the optimized dosimetry plan, a prostate volume study using the transrectal ultrasound probe is an important step for successful execution of the brachytherapy procedure. In the volume study, the patient lies on his back, the ultrasound probe is inserted into the rectum with the aid of a stabilizing or stepper apparatus and transverse cross-sectional images of the prostate are acquired at fixed intervals, e.g., 5 mm increments from the base (superior) of the gland to the apex (inferior). Currently, the prostate boundary is manually outlined by a clinician in each transverse cross-sectional ultrasound image. The overall volume of the prostate is determined using well-known step section planimetric techniques. The boundaries of the prostate obtained during the volume study not only result in an accurate determination of the size and shape of the prostate, but also provide important information for developing the radiation dosimetry plan. The end result of the computerized dosimetry plan is an accurate map for placing the seeds within the gland.

The ultrasound probe, which is inserted in the patient's rectum, is used to obtain the transverse cross-sectional images of the prostate during the initial prostate volume study. Though the transrectal ultrasound provides a better quality image of the prostatic tissue than CT and MRI, the visibility of the prostate boundaries is typically poor for the following reasons:

(1) The pelvic musculature and rectal wall generate strong echoes, which result in linear artifacts in the images, which give the false appearance of a boundary.

(2) The incident ultrasound beam is scattered in random directions, producing artifacts, such as missing edges.

(3) The top part of boundary is positioned at a considerable distance from the ultrasound probe and, hence, greater attenuation of the ultrasound energy results in poor contrast.

(4) The boundary located in the far field of the ultrasound image is greatly degraded due to much lower contrast.

(5) Part of the boundary is outside of the imaging window so that they are invisible in the transverse section images.

To overcome such deficiencies, typically, the practitioner must manually draw the prostate and rectum boundaries. The manual drawing of the prostate and rectum boundaries takes a longer time than is desirable (nearly 10–20 minutes for a whole series) and brings inconvenience to the operation. Also, each clinician will give different definition of the prostate boundary because of the various experiences and knowledge; that is, drawing prostate boundaries is user-dependent.

SUMMARY OF THE INVENTION

It will be readily apparent from the above that a need exists in the art to reduce the time requirement and subjectivity in the determination of prostate and rectum boundaries. It is therefore a primary object of the present invention to provide accurate, stable, and automatic segmentation of prostate boundaries prior to beginning the seed implant procedure.

To achieve the above and other objects, the present invention includes a method for determining the prostatic boundaries, the rectum edge and the urethra on transrectal ultrasound images. An ultrasound image of a transverse cross-sectional outline of the prostate gland is acquired. For three-dimensional imaging, a series of images can be taken, one of each slice of the prostate. The initial ultrasound images are pre-processed to remove the noise and increase the contrast. The rectum edge is located from the bottom of the images. The key points on the prostate boundaries are located and connected under the iterative training of a knowledge-based model until the shape of the boundary reaches a stable state. The urethra is segmented near the center of the prostate.

In the present invention, the previously-used manual drawing to produce the prostate boundaries is eliminated, and the initial image produced by the ultrasound probe is automatically processed in a series of steps to create an accurate segmentation of the rectum edge, prostate boundary, and urethra edge. Then the algorithm will overlay the detected boundaries relative to the transverse cross-section of the prostate to provide important information for dosimetry planning.

The automated image segmentation of the present invention will reduce the median operative time for anatomy delineation for intraoperative planning, from 10 min. to 2 min. for complete outline of the prostate, urethra and rectum. The original image is provided by the ultrasound probe and a traditional stepper. The image is then processed to extract an outline of the prostate boundary.

BRIEF DESCRIPTION OF THE DRAWINGS

A preferred embodiment of the present invention will now be set forth in detail with reference to the drawings, in which.

DETAILED DESCRIPTION OF THE PREFERRED EMBODIMENT

A preferred embodiment of the present invention will be set forth in detail with reference to the drawings. First, an overview of the process will be set forth. Then, individual steps will be described in greater detail. Finally, a system for implementing the preferred embodiment will be shown.

Figure 1:
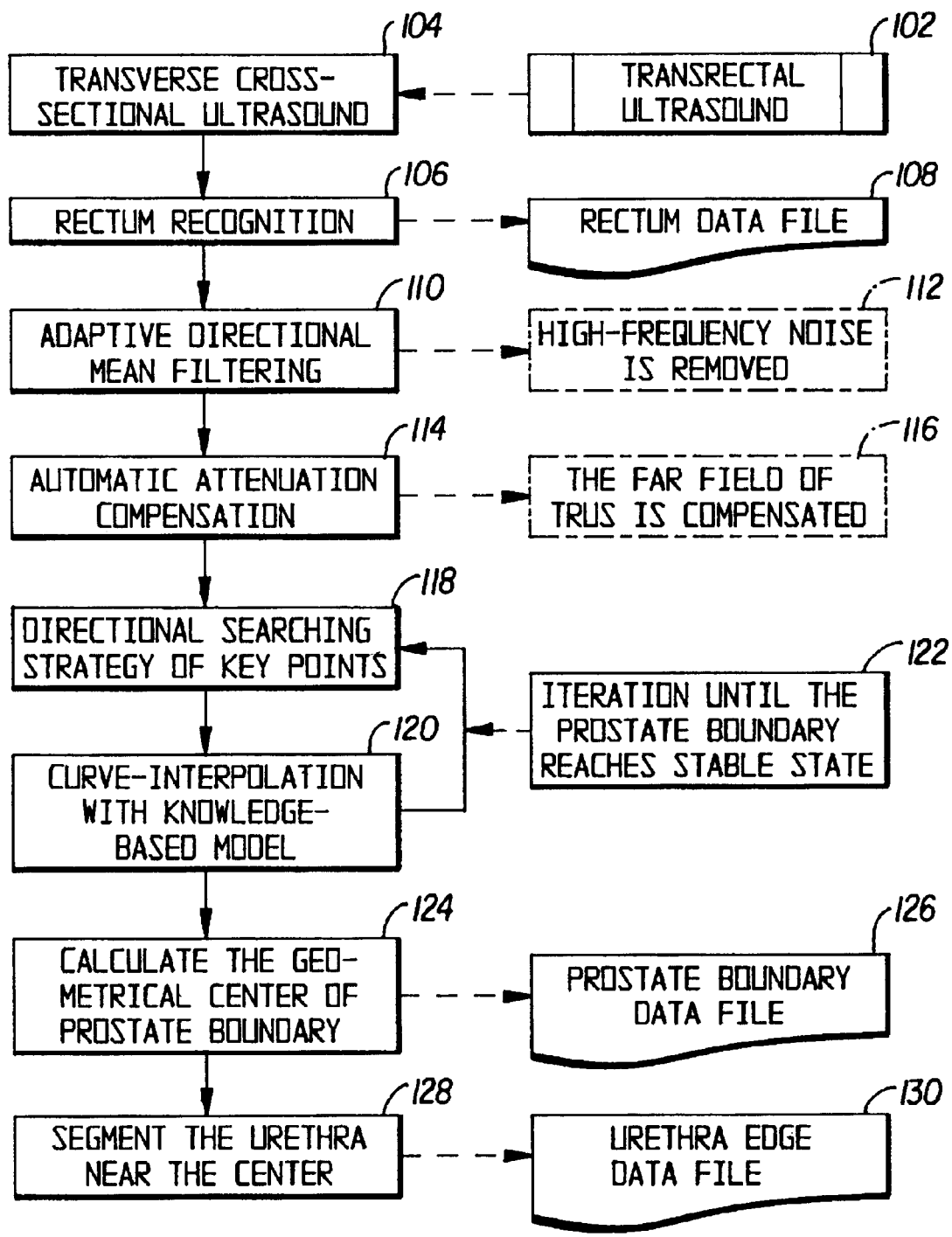
FIG. 1 is a simple flow chart showing the steps in segmenting of prostate boundaries obtained by an ultrasound probe.

As shown in FIG. 1, the process begins with the taking of a transrectal ultrasound image in step 102. If a 3D model of the prostate is to be formed, multiple transrectal ultrasound images can be taken to reconstruct the three-dimensional shape of the prostate from multiple slices of the prostate. The result is a transverse cross-sectional ultrasound image of the prostate in step 104.

Figure 2A:
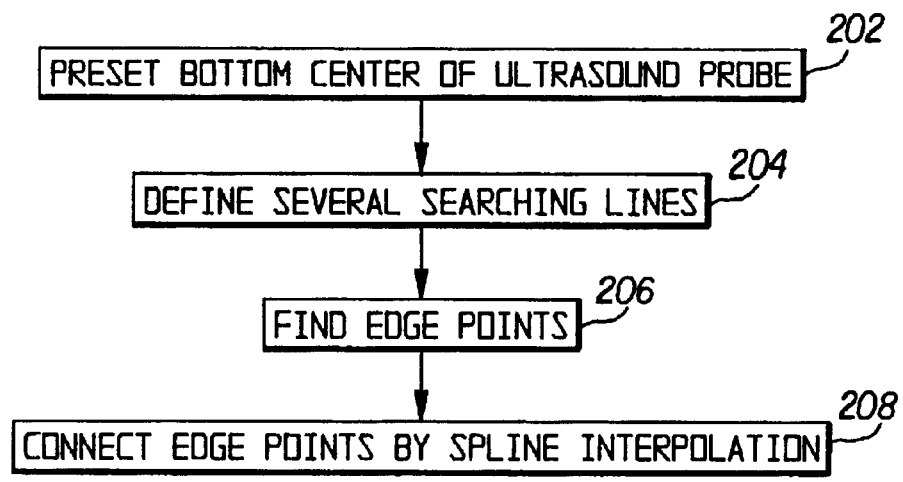
FIG. 2A shows a flow chart of the operations for recognizing the rectum edge.
Figure 2B:
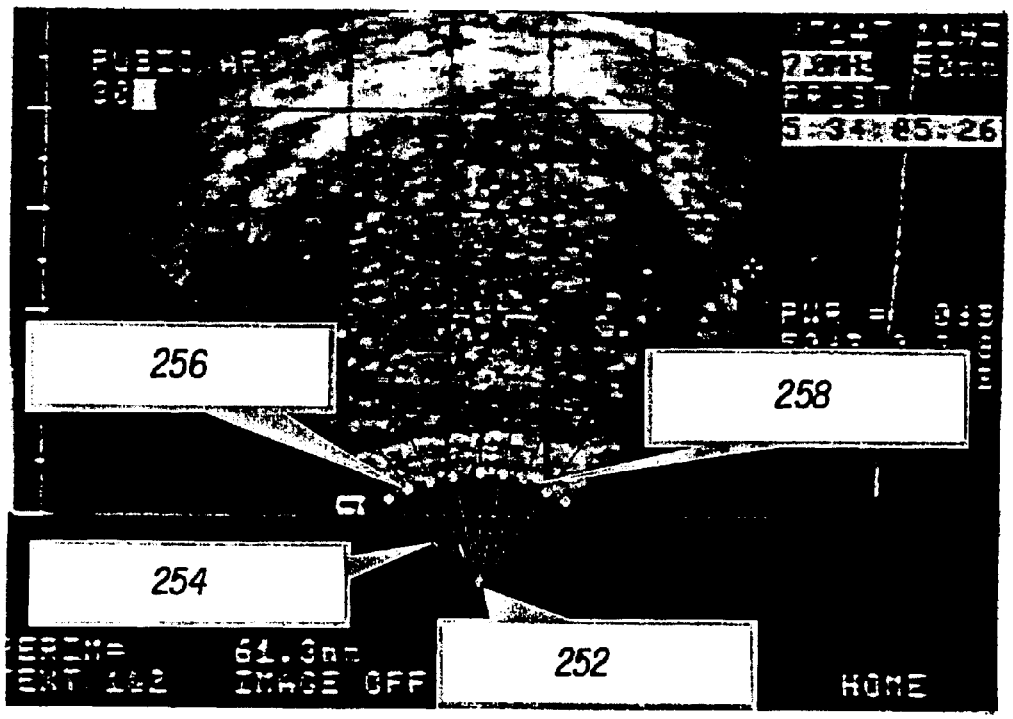
FIG. 2B shows a result of the recognition operations of FIG. 2A.

The edge of the rectum is recognized in step 106, in a manner to be set forth below with references to FIGS. 2A and 2B. The result is stored in a rectum data file in step 108.

The image is filtered through adaptive directional mean filtering in step 110 to remove high-frequency noise as indicated in step 112. The specifics of the adaptive directional mean filtering will be set forth below with reference to FIGS. 3A–3C.

Since attenuation of the ultrasound waves increases away from the ultrasound probe, such attenuation is compensated for in step 114 to obtain an image for which the far field is compensated in step 116. Details of the compensation will be set forth below with reference to FIGS. 4A and 4B.

Then, the boundary of the prostate is located. Key points are found in step 118, and a knowledge-based model is used to fit a curve in step 120. Steps 118 and 120 are iterated until the boundary reaches a stable state in step 122. The location of the boundary will be set forth below with reference to FIGS. 5A and 5B.

The geometrical center of the prostate boundary is found in step 124 and is stored in a prostate boundary data file in step 126. The urethra is segmented near the center of the prostate in step 128, and its edge is stored in a urethra edge data file in step 130. The process of segmenting the urethra will be explained below with reference to FIG. 6A, and the end result will be described with reference to FIG. 6B.

Rectum recognition will now be described with reference to FIGS. 2A and 2B. The rectum edge is recognized from the transrectal ultrasound image. Rectum segmentation is realized by low gray-scale thresholding and spline-interpolation methods. The first edge from the bottom center of the images is defined as the rectum boundary. To simplify the algorithm, the following strategy is used:

Preset the bottom center 252 of the transrectal ultrasound probe, which is a constant in a given system (step 202);

Define several searching lines 254 from the bottom center at special angles (step 204);

In every line, find the edge point 256, which is the first point at which the gray-scale is greater than a threshold value and the first derivative of the gray scale is greater than zero (step 206); and These edge points 256 are connected by a spline-interpolation method to form an interpolated curve 258 of the edge of the rectum (step 208).

Figure 3A:
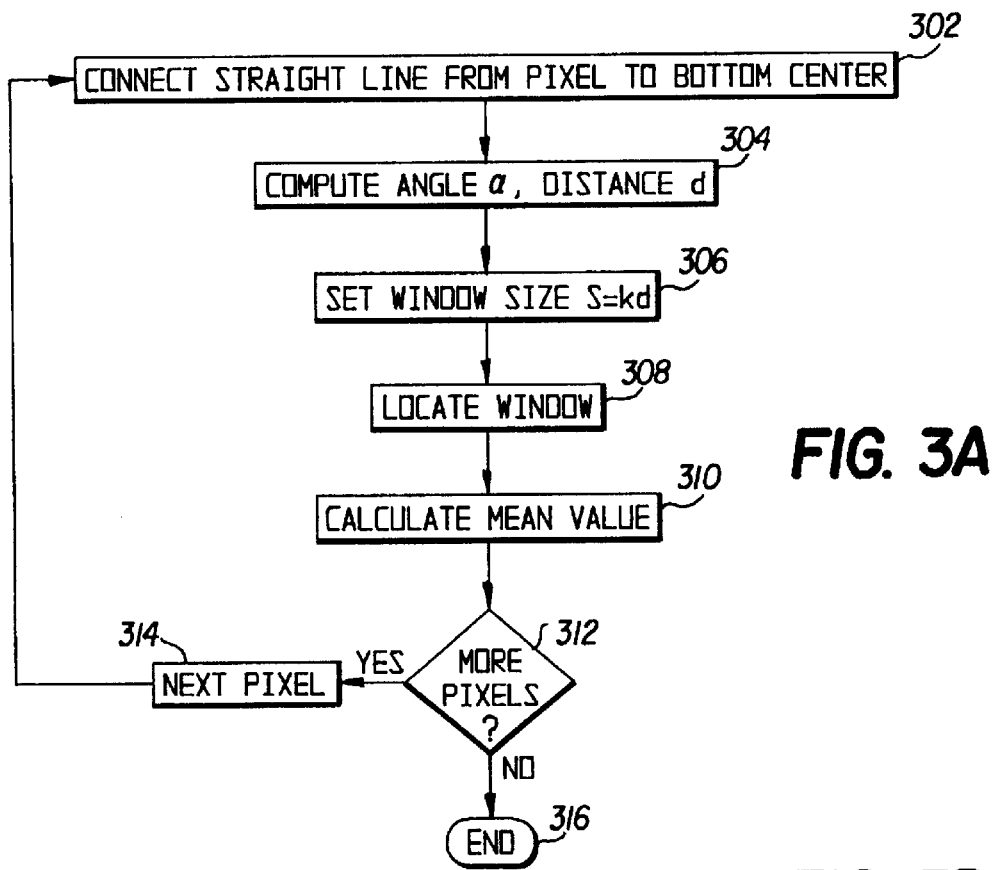
FIG. 3A shows a flow chart of adaptive directional mean filtering to cut down the high-frequency noise in the images.
Figure 3B:
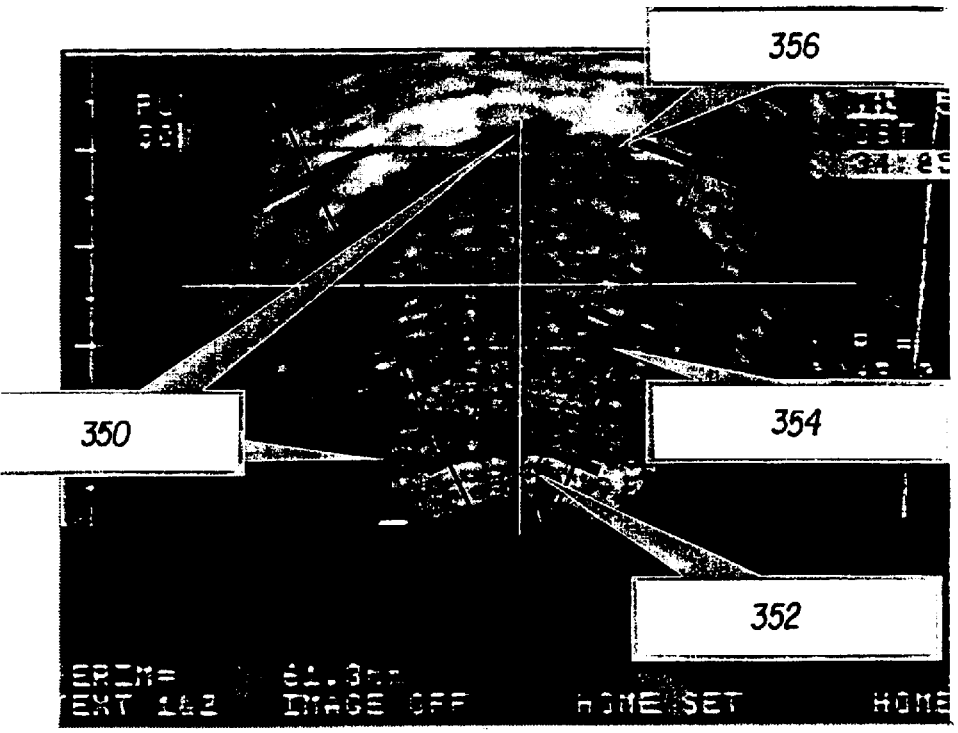
FIG. 3B shows a result of the filtering of FIG. 3A.
Figure 3C:
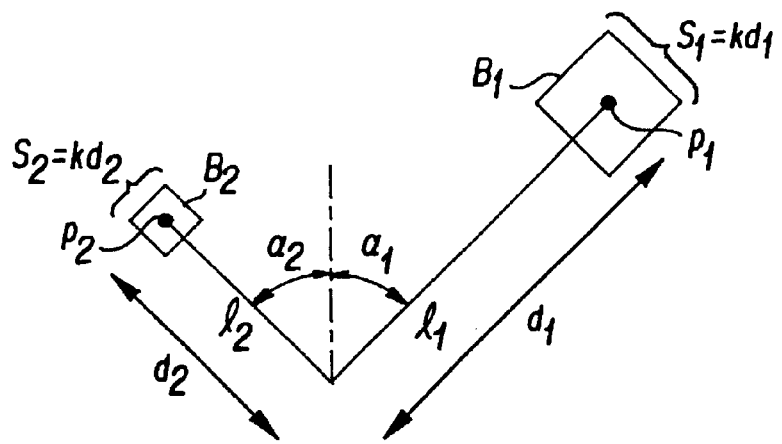
FIG. 3C shows the formation of windows in the filtering of FIG. 3A.

In the directional adaptive mean filtering of FIGS. 3A–3C, the ultrasound image is enhanced by a noise removal technique. In this step, Gaussian filtering and traditional mean filtering could be used, but these are not the best solutions for this problem. The difficulty is the blurring edges between these tissues, which are caused by the artifacts and unstable digitization of ultrasound. Gaussian filtering requires an unacceptably long time to run. The traditional mean filtering uses a constant rectangle mask in filtering the images, which will introduce distortion to the prostate boundaries. At the same time, the complexity of structure definition and the low speed of texture analysis are unfeasible for real-time operation.

To overcome those difficulties, the preferred embodiment implements a directional adaptive mean filtering method, which retains the merits of the fast algorithms such as mean filtering and adaptive window filtering. The speed is higher thank of the Gaussian filtering method.

The following steps shown in FIG. 3A are carried out for every pixel. In step 302, a straight line is connected from the pixel to the bottom center. In step 304, the angle α of the line and the distance d between the pixel and the bottom center are calculated. In step 306, the window size around the pixel is set to be s=kd, where k is a positive constant. In step 308, a window of mean filtering is located on the image, wherein the center of the window is the pixel and the window is perpendicular to the straight line. In step 310, the mean value throughout the window is calculated, and the value of the gray scale at the pixel is reset to that mean value. In step 312, it is determined whether there are more pixels to be processed. If so, the process proceeds to the next pixel in step 314. Otherwise, the process ends at step 316.

In FIG. 3B, the filtered images show that the high frequency noise is removed and the original edge information 350 is protected from the distortion. Because this algorithm utilizes the important characteristics about directional diffraction and far field attenuation of the B-mode ultrasound signals, an optimized filtering is reached and the filtered images will be more easily used in the subsequent processing steps.

The window increases in size away from the bottom center. FIG. 3C shows a first line $l_1$ drawn between the bottom center BC and a first pixel $p_1$ and a second line $l_2$ drawn between the bottom center BC and a second pixel $p_2$. The first line $l_1$ has a length (distance) $d_1$ and an angle $\alpha_1$, while the second line $l_2$ has a length (distance) $d_2$ and an angle $\alpha_2$. The pixel $p_1$ has a box $B_1$ drawn around it with a size $s_1=kd_1$, while the pixel $p_2$ has a box $B_2$ drawn around it with a smaller size $s_2=kd_2$. The windows of increasing size are shown in FIG. 3B as 352, 354 and 356. The windows do not have to be square.

After the filtering, the filtered image is enhanced by an automatic attenuation compensation method, which will now be described with reference to FIGS. 4A and 4B. That method is designed for commonly observed situations in which manual adjustment cannot fully compensate the greater attenuation in the far field of the ultrasound images. In FIG. 3B, the far field of the left and right part is invisible and the boundary in that area is very fuzzy because of the much lower brightness. To overcome this problem, the preferred embodiment implements an automatic attenuation compensation method by assuming a specified relationship between local attenuation and local backscatter throughout each pulse-echo signal, thus determining a gain factor that more appropriately compensates for attenuation at each depth.

Figure 4A:
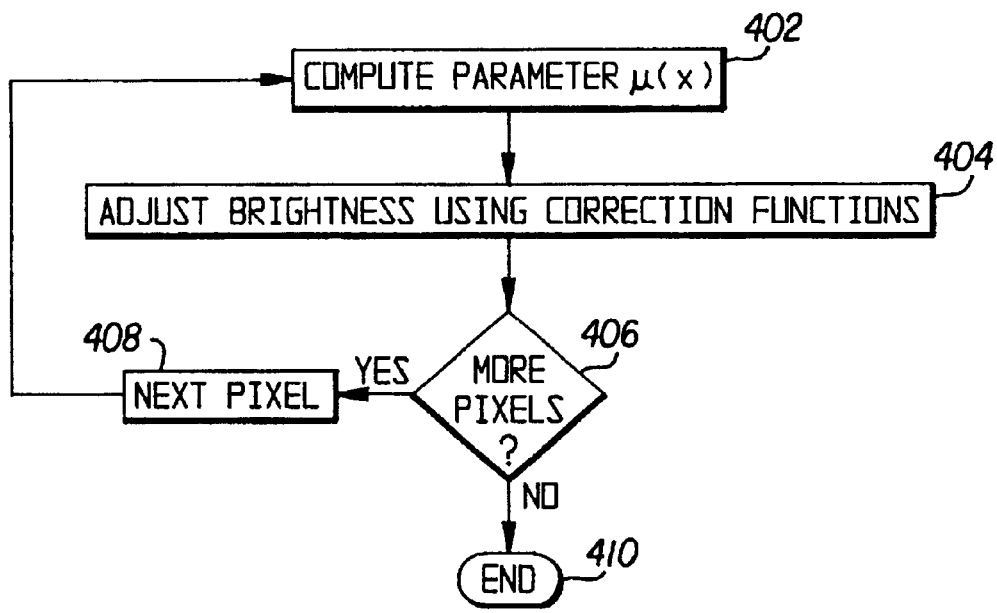
FIG. 4A shows a flow chart of an automatic attenuation compensation method to improve the far field compensation in the transrectal ultrasound images.

For each pixel, the following operations shown in FIG. 4A are performed. In step 402, the following parameter is computed:

$$\mu(x) = \frac{R(x)e^{2Ax}}{\sum\limits_{x}^{\infty} R(i)e^{2Ax}},$$

where R(x) is the gray-scale value at the position x of the pixel. A has a value selected in accordance with the relationship between local attenuation and local backscatter noted above.

In step 404, the brightness is adjusted by one of the following formulae:

$$R(x) = R(x)\mu(x) \times (p) \quad \text{(function 1)}$$

$$R(x) = \mu(x) \times (q) \quad \text{(function 2)}$$

Here, p and q are additional parameters which can be varied to adjust the transformed pixel to have a better visible effect.

In step 406, it is determined whether there are any more pixels to process. If so, the process advances to the next pixel in step 408. Otherwise, the process ends at step 410.

Function (1) has a better result than function (2) overall, especially in dark images. But function (2) has better results in the far field than function (1). Function (2) can be used exclusively to improve the image quality of the far field, or functions (1) and (2) can be combined in both near field and far fields.

Figure 4B:
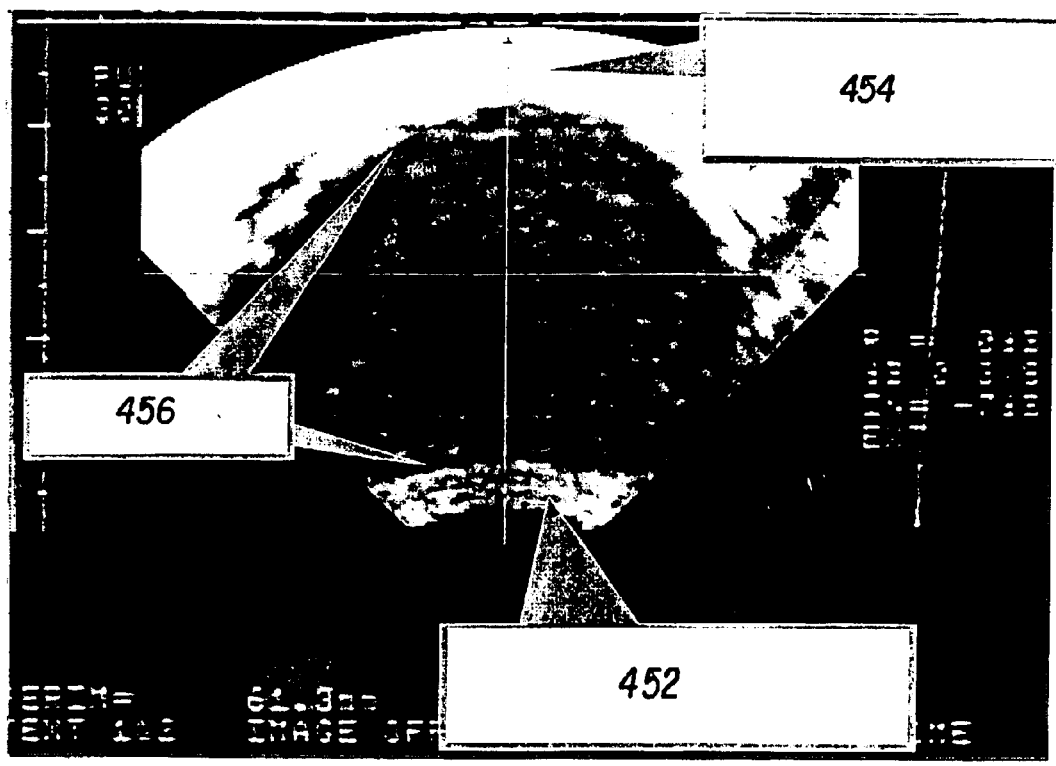
FIG. 4B shows a result of the attenuation compensation of FIG. 4A.

In FIG. 4B, the compensated image shows that while little compensation is required in the near field 452, the far field 454 of the transrectal ultrasound image, especially the dark area, is enhanced into a bright background. The original prostate boundaries 456 are enhanced, and the original position information is protected without inducing false edges.

Once the ultrasound image has been enhanced by the noise removal technique and the automatic attenuation compensation method as described above, the image is segmented, as will be explained with reference to FIGS. 5A and 5B. Conventional methods of segmenting an object edge from an image are based on detecting step discontinuities in gray scale (brightness). In some cases, angular information of an edge is used by calculating the angle from the neighbor area of a particular pixel in the image. In ultrasound images, such conventional segmentation methods are not appropriate due to the poor signal to noise ratio, as well as speckle noises. Also, when conventional edge detection algorithms are applied to detect edges of ultrasound images, they generate an excessive number of false edges.

To overcome those difficulties, edge detection using a directional search strategy plus knowledge-based modeling is used as opposed to a discontinuity approach. From the center of the images, as shown in FIG. 5B, the algorithm searches several specific angular orientations 552 from the center 554, and reads the data into a one-dimensional array. In every data line, the algorithm selects a key edge point 556 that is most likely to represent the edge between the prostate and normal tissue in the lines. That key edge point 556 divides the data line into two parts that have the largest difference in gray-scale distribution. The algorithm calculates the curve-fitting with these key points under the iterative training of a knowledge-based model until a stable prostate boundary 558 is obtained.

Figure 5A:
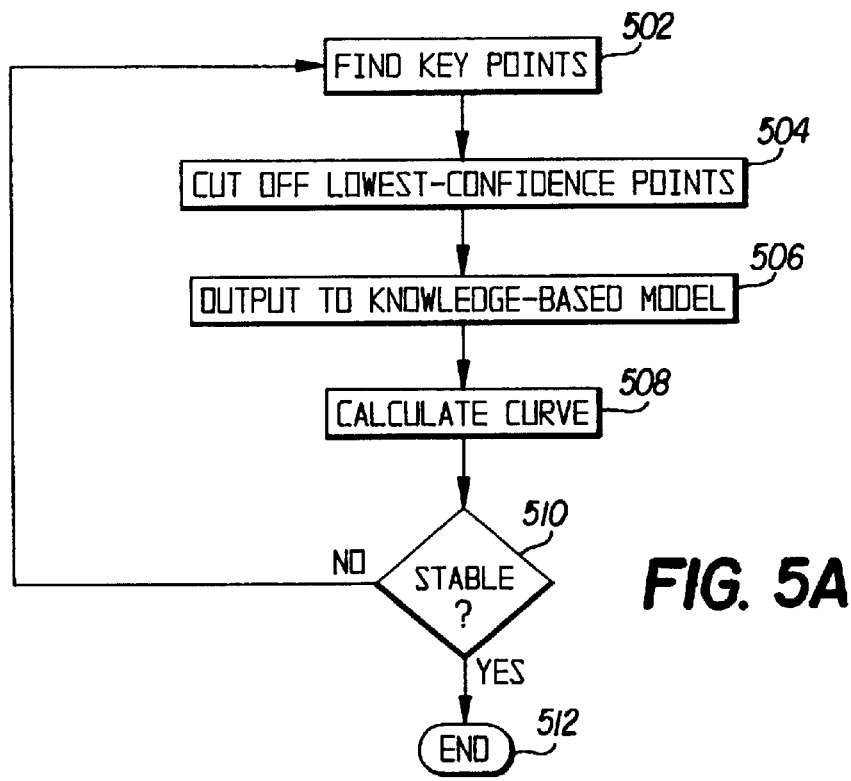
FIG. 5A shows a flow chart of operations used in locating the prostate boundaries using a knowledge-based model.

The directional search strategy and model-supervision training is described by the following steps shown in FIG. 5A:

Step 502: finding the key points.
    Loop all directions (Currently 21 orientations are selected)
    {
        In every direction, three lines are processed, including angle, angle+delta, angle−delta.
        {
(1) calculate the length of the current line
(2) calculate the angle of this current line from the center position
(3) read the line data into an array
(4) calculate the entropic threshold in this line (5) enhance the difference in this data line by gray-scale transformation defined by entropic threshold
(6) obtain the segmentation point by loading HANBET method
{

HANBET Method Definition calculate the whole mean and variance of the data line
check the start and end situation as the reference of prostate & tissue
mean-filtering of the data line
find the maximum & minimum value in the mean-filtering data
find the whole mean and variance of the data line
calculate the entropic threshold in this line
searching from begin to end in the data line
{
 get the mean value of the inner data
 get the mean value of the outside data
 calculate the variance between inner and outer
}
get the maximum variance to determine the best threshold
erase the inner/outer error of the computation
return the segmentation point and the confidence
 }
 }
 }
 Select the best segmentation to overcome the noise disturbance.
}
Step 504: Cut off the lowest confidence key points (those whose confidence level is below a predetermined threshold).
Step 506: Output the key points to the knowledge-based model.
Step 508: Calculate the curve under the instruction of the knowledge-based model, which is trained by a database of prior cases.
Steps 510 and 512: Iteratively run Steps 502–508 until a stable center of prostate boundaries is reached. That is, the distance between two repeatedly calculated prostate centers will be less than a preset threshold.

Figure 7A:
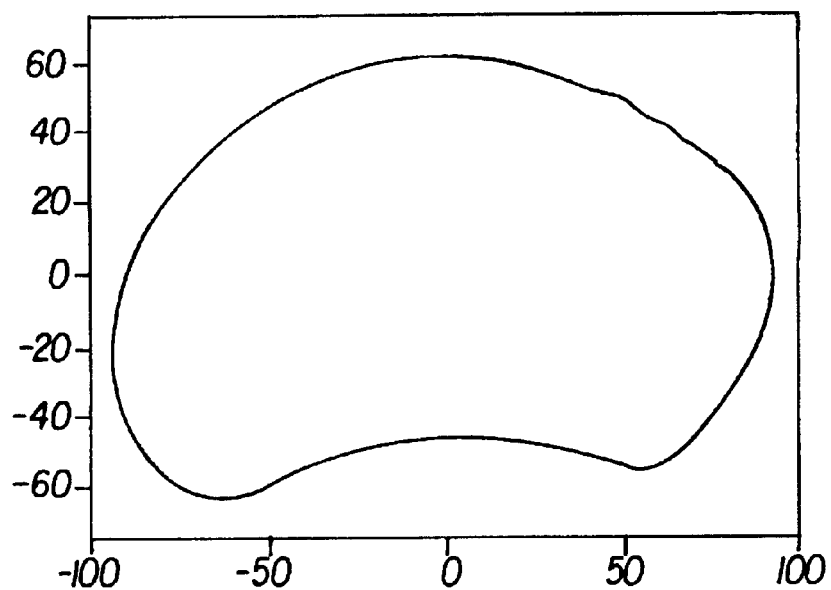
FIGS. 7A and 7B show a 2D model of a prostate boundary.
Figure 7B:
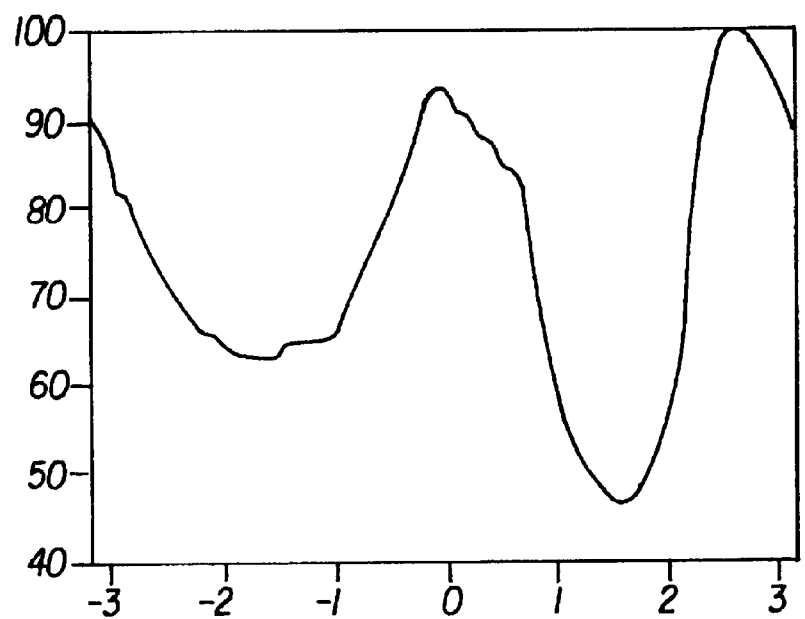

In training the prostate 2D boundary model and 3D surface model process, a large number of pre-defined prostate shapes are input as training samples. The 2-D shapes of the boundary in the X-Y coordinates are extended to curves in the polar coordinates. An example is shown in FIGS. 7A and 7B, which FIG. 7A shows a typical boundary shape of a central slice of a prostate, and FIG. 7B shows the extension result in the polar coordinate system, where the horizontal coordinate is the angle in radians from $-\pi$ to $+\pi$, and the vertical coordinate is the distance from the center point (0,0) in FIG. 7A to the points on the boundary. In polar coordinates, since the horizontal coordinates are all the same for all training samples, each sample can be represented by only a set of vertical coordinate values in the form of a vector (suppose N×1 in size).

So we can get L training sample vectors if we have L pre-defined boundaries of prostate. From the L training sample vectors, we first calculate their average vector Average_Vector by $$\text{Average\_Vector} = \frac{\sum_{i=1}^{L} (\text{Sample\_Vector})}{L},$$

and then calculate the Eigen-vectors and Eigen values of the normalized sample matrix Normalized_Sample_Matrix=[(Sample_Vector)$_i$–Average_Vector]$_{i=1\ to\ L}$ Then select the Eigen vectors corresponding to the M top largest Eigen values (M<Minimum(N, L)), and construct an Eigen matrix Eigen_Matrix.

Retrieval Equation:

Retrieval_Vector=Average_Vector+Eigen_Matrix×Weight_Coefficiency in which, Retrieval_Vector and Average_Vector are column vectors of N×1, where N is the number of points to be retrieved. Eigen_Matrix is a matrix of N×M, where M is the number of points used to retrieve the whole information. Weight_Coefficiency is a column vector of M×1. It provides the weights to each column of Eigen_Matrix.

This equation is used to retrieve a set of N points from another set of M points, which is much smaller in size. The Average_Vector and the Eigen_Matrix are pre-determined by the training process. They contain most of the information of the training set. Once a Weight_Coefficiency is given, a Retrivieval_Vector can be calculated from this equation.

The weights can be calculated by solving the solution of a set of linear equations Weight_Coefficiency=(Eigen_Matrix)/(Retrieval_Vector–Average_Vector), Since we only need M equations to set the M×1 vector Weight_Coefficiency, we can use M key points to calculate the weights by Weight_Coefficiency=(Eigen_Matrix)\(Key_Points_Vector–Average_Vector_Select)

in which Key_Points_Vector is an M×1 vector that only contains the coordinate values of M key points, and Average_Vector_Select is also an M×1 vector that only contains M values in the Average_Vector at the corresponding position to that of key points.

The selection of the key points is a matter to be considered. It is the position, rather than the number of the key points, which is more critical to the quality of the retrieval shape. The key positions lie in the positions with greater variations, such as the positions on about 0, $\pm\pi/2$, etc.

The function of the model can be described as connecting the already known key points according to a similar shape in the training set. The Average_Vector provides an average shape of the training slices, and the Eigen_Matrix×Weight_Coefficiency provides the variances of the given shape to the average shape. The key points are detected by the previous-described grayscale based boundary detection algorithm. If the key points found by the previous step are all accurate, the connecting function of the model will be just like a curve fit by using the spline method. But if several points found in the previous step are not correct, for example, clearly projecting inside or outside, the spline method will fit the curve exactly along the key points so that the whole shape of the boundary will project inside or outside, while the model can correct this clear mistake by retrieving it to a similar prostate shape. Of course, if many key points are wrong, the model will give a wrong shape.

Figure 8A:
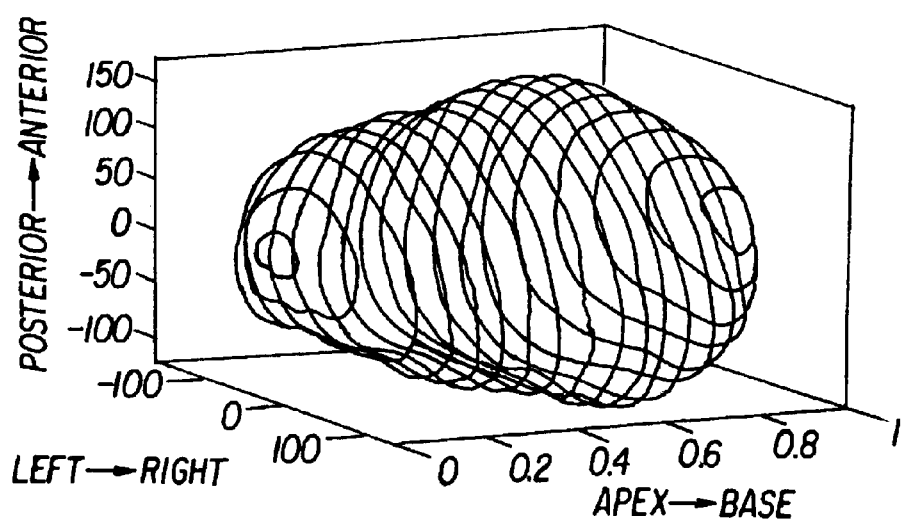
FIGS. 8A and 8B show a 3D model of a prostate volume.
Figure 8B:
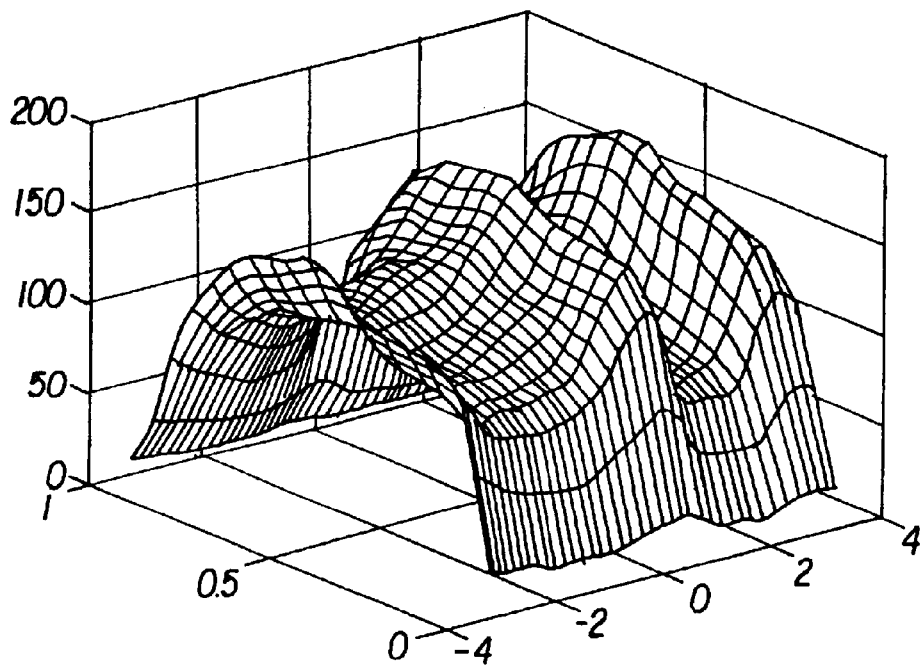

Similar to the 2-D model, 3-D model uses the pre-defined shapes of boundaries of a series of image slices of a prostate as its training samples and retrieval objects. FIG. 8A shows an example. When it is extended using the polar coordinate system, it will be a surface like FIG. 8B. The x-coordinate represents the normalized length of a prostate from apex to base, the y-coordinate represents the polar angle of the shape in each slice, and the z-coordinate represents the distance of the boundary to the center of each slice. Since the x-coordinate and the y-coordinate of the surface are the same to all the training samples, the z-coordinate data on the surface can make a sample vector used as training vectors. And the training and retrieval process described in the 2-D model section can be used here.

The construction of the 3-D model needs more training samples because the total data volume of each training sample has increased T times, where T means the normalized number of slices along the apex to base direction. In other words, the prostate is cut into T slices from apex to base, each section has its own boundary while the whole prostate has T such 2-D boundaries.

For most original image series of the prostate, the slices in the apex and base areas have no clear boundaries to be defined, and the size tapers off dramatically. So in each sample, we add a small circle before the apex and after the base, so that the 3-D prostate sample can converge at two ends.

Figure 5B:
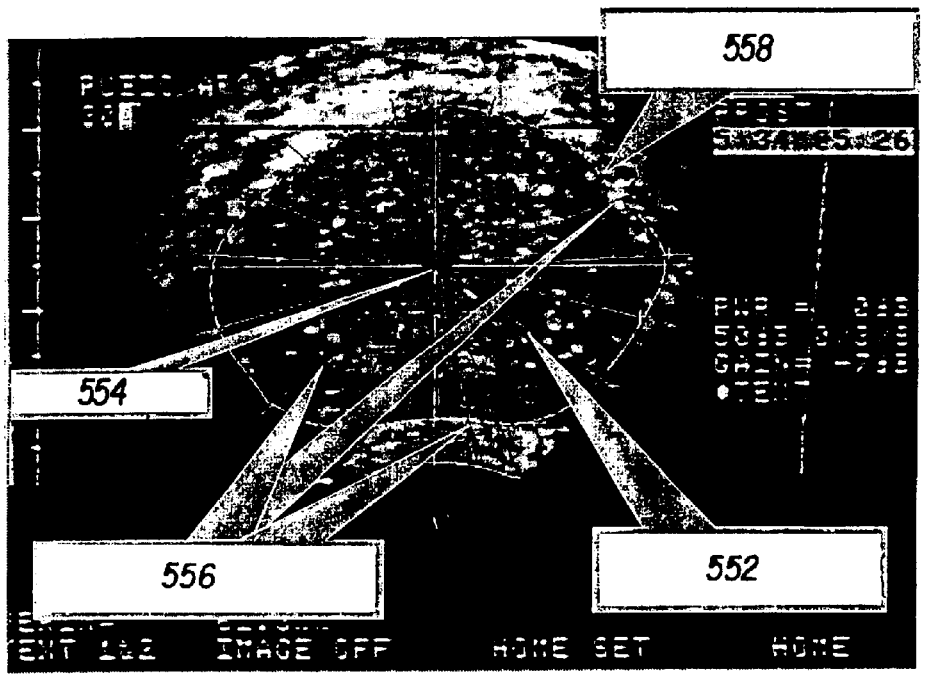
FIG. 5B shows a result of the prostate boundary location of FIG. 5A.

FIG. 5B shows that the segmented boundaries match with the original prostate image.

Figure 6A:
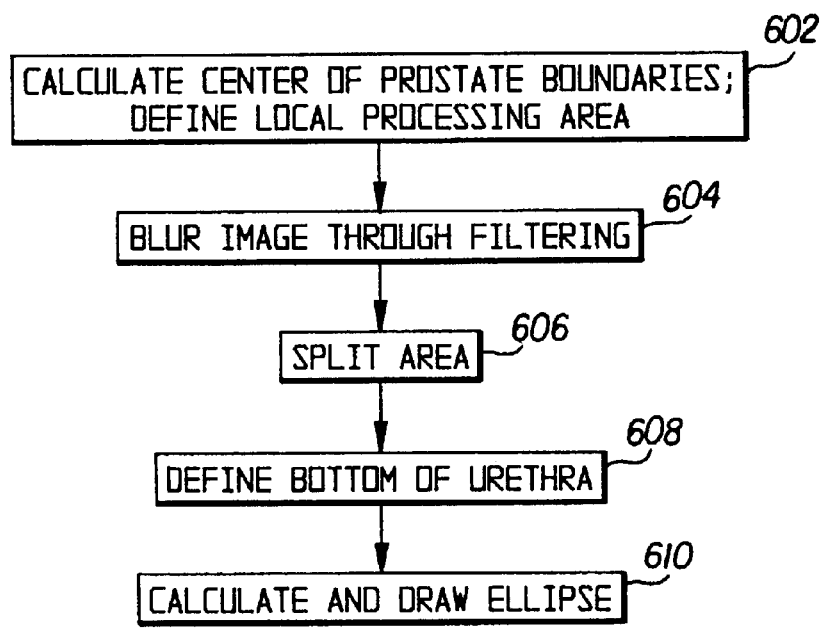
FIG. 6A shows a flow chart of operations used to locate the urethra.

After finding the prostate boundaries, the geometrical center of the prostate boundaries is calculated by a weight-averaging method, and then the urethra is located in a manner which will be explained with reference to FIGS. 6A and 6B. Usually the urethra is located near the center of the prostate or more anteriorly. Typically the urethra will be localized as a strong reflection object because of the insertion of the urethra catheter or contrast. The strong reflection of the urethra catheter or contrast will introduce a disturbance in the local area, such as a bright spot with a long dark shadow. By using this specific information, we define the following algorithm in finding the urethra edge:

Calculate the geometrical center of the prostate boundaries and define a local processing area around this center (step 602).

Run Gaussian filtering or fast mean filtering in this small area to greatly blur the image (step 604).

In the local area, find the position of a horizontal line which splits the area into two parts that have the largest difference in gray-scale distribution (step 606). The top part will have lower gray-scale value than the bottom part. The difference can be defined as the mean, or standard-derivative.

Define the internal part of the splitting line as the bottom of the urethra (step 608)

Calculate an ellipse, which has a ratio of long axis to short axis equal to 1.5 and the length of the long axis is the same as the length of the internal line; draw the ellipse on the screen and let the bottom of the ellipse match the internal line (step 610).

Figure 6B:
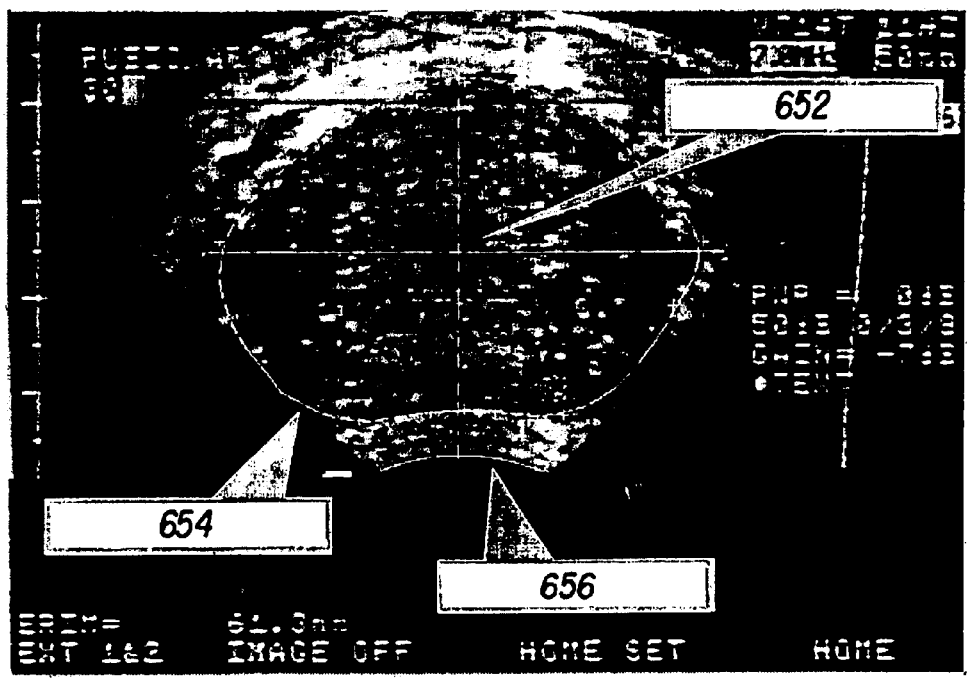
FIG. 6B shows a final result of prostate boundary, rectum edge and urethra edge location according to the operations of FIGS. 2A, 3A, 4A, 5A and 6A.

In FIG. 6B, a final drawing of the urethra edge 652 is given. To illustrate the whole procedure of the algorithm, the prostate boundary 654 and rectum edge 656 are also overlaid on the image. At this point, automatic segmentation of the ultrasound image is completed. The segmented boundaries may be manually edited using common drawing tools, if so desired.

The above-described automatic segmentation technique has been evaluated experimentally. In the experimental bench test protocol, the initial transverse cross-sectional images of the prostate were obtained with a Siemens ultrasound machine, a B&K machine and an Acuson machine. After the prostate images were processed and detected, the rectum, urethra and prostate boundaries were overlaid on top of the transverse cross-sectional image of the prostate. The mean success rate was 80% for the internal slice images (i.e., excluding the apex and base images), which indicates that the process of the present invention on the average predicts the location of the prostate boundaries correctly for approximately 7–8 out of the 10 images. The mean error rate of the present process is due to special situations such that the left/right bottom of the prostate is outside the field-of-view on the images, in which case no gold standard exists for judging the correctness of the prostate boundary in that corner. This small error rate can be remedied by additional manual editing, and the total time cost will also be far less than the whole manual drawing procedure.

The determination of prostate boundaries in patients undergoing prostate rachytherapy is a critical part of the overall brachytherapy procedure. The above-identified process permits identification of prostate boundaries using the transrectal ultrasound probe with little additional time and effort.

The above-described processing sequence can be carried out in a portable or desktop computer that has a frame grabber to digitize the analog images. When the above-described process is accomplished on an external PC-based workstation linked to the ultrasound machine, which digitizes the ultrasound video output from the ultrasound probe, prostate boundaries can be segmented interactively during the whole operation.

Figure 9:
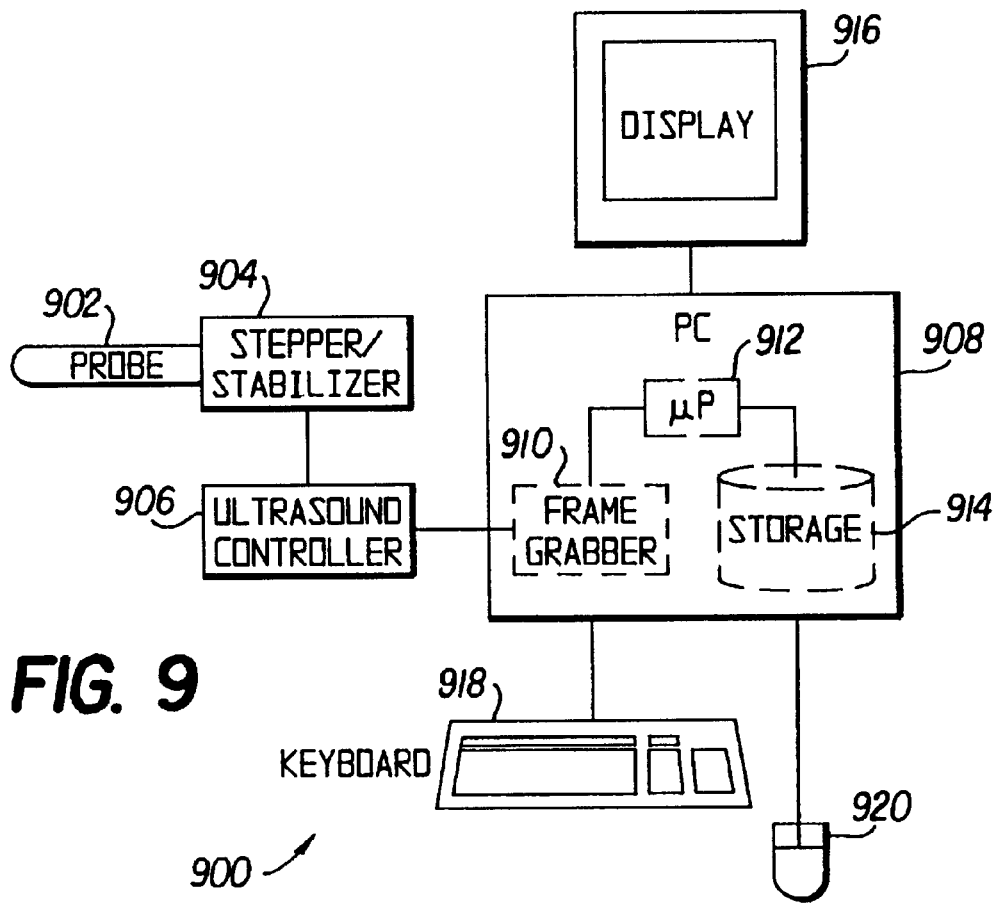
FIG. 9 shows a schematic diagram of a system on which the preferred embodiment an be implemented.

More specifically, a system on which the preferred embodiment can be implemented is shown in FIG. 9. As shown in that figure, the system 900 includes an ultrasound probe 902 which is positioned in the patient with a stepper or stabilizer 904 under control of the physician through an ultrasound controller 906. The ultrasound controller 906 transfers data to a computer 908, such as an IBM-compatible microcomputer or any other computing device capable of performing the processes set forth above. The computer 908 includes a frame grabber 910 to convert raw image data received from the ultrasound controller 906 into digital format for use in the computer 908; frame grabbers are known in the art and typically take the form of cards to be inserted into expansion slots on the motherboard of the computer 908. The computer 908 also includes a microprocessor 912 and storage 914, such as a hard drive, for storing both the program code for implementing the processes described above and the resulting data files. The computer 908 provides a user interface to the physician with suitable input and output devices, such as a display 916, a keyboard 918 and a mouse 920. Alternative devices, such as trackballs and light pens, could be used as needed.

Ultrasound image acquisition is well known, as is the equipment used to perform it. Three exemplary types of transrectal ultrasound machines used in interstitial brachytherapy are Siemens, Acuson and B&K. The present invention has been tested and proved effective in imaging generated by all such known ultrasound machines.

The boundary detection algorithms described above will be used before the seed implant procedure. During the operation procedure, needles will be inserted into the gland and there will exist many hyper-echoic spots from bleeding and needles. This will affect the boundary detection algorithm because the grayscale difference between the inner gland and the outside tissue will be much smaller than the grayscale difference between the highly bright hyper-echoic spots and the other areas. So in order to continue to be able to detect the boundary effectively during the seed implant procedure, two additional steps were added into the methods. The first is noise removal. Since the areas of the hyper-echoic spots are small, they can be considered as point noises and removed by smoothing processing. The other is interest point removal based on the seed detection algorithm. The hyper-echoic points representing seeds will be detected during the implant procedure. Then the grayscale level within the related area around those points will be reduced to their background so that there will be no highly bright points within the prostate boundary. Thereafter, the methodology described herein can be applied to the ultrasound image.

While a preferred embodiment of the present invention has been set forth above in detail, those skilled in the art who have reviewed the present disclosure will readily appreciate that other embodiments can be realized within the scope of the invention. For example, the algorithm described above can also be used for other types of ultrasound images such as trans-urethra ultrasound images, or the images obtained by any type of ultrasound machines such as Acuson, Siemens, B&K, and ATL, etc. It also can be used for boundary detection in the images of other human organs, such as the liver. For that matter, it is not limited to human organs at all. Therefore, the present invention should be construed as limited only by the appended claims.

What is claimed is:

1. A method of determining boundaries of an object, the method comprising:
   (a) acquiring an image of a transverse cross-sectional outline of the object;
   (b) pre-processing the image acquired in step (a) to remove noise and increase contrast so as to produced a pre-processed image;
   (c) finding an edge of the object from a point in the pre-processed image; and
   (d) locating key points of the boundaries of the object and connecting the key points under iterative training of a knowledge-based model until a shape of the boundaries of the object reaches a stable state.

2. The method of claim 1, wherein the object comprises at least one organ of a living being.

3. The method of claim 2, wherein the living being is a human being, and wherein the at least one organ comprises a prostate or a urethra of the human being.

4. The method of claim 3, wherein step (a) comprises using ultrasound.

5. The method of claim 4, further comprising (e) segmenting a possible location of the urethra near a center of the prostate.

6. The method of claim 5, further comprising (f) forming a model of the prostate from the shape of the boundaries determined in step (d).

7. The method of claim 6, wherein the model formed in step (f) is a two-dimensional model.

8. The method of claim 6, wherein the model formed in step (f) is a three-dimensional model.

9. The method of claim 8, wherein each of steps (a)–(e) is performed a plurality of times to take a plurality of slices of the prostate to form the three-dimensional model.

10. The method of claim 3, wherein the at least one organ further comprises a rectum of the human being, and wherein the method further comprises segmenting a possible location of an edge of the rectum.

11. The method of claim 1, wherein each of steps (a)–(d) is performed a plurality of times to take a plurality of slices of the object.

12. The method of claim 11, further comprising forming a model of the object from the shape of the boundaries determined in step (d).

13. The method of claim 12, wherein the object is an organ of a living being.

14. The method of claim 13, wherein the living being is a human being.

15. The method of claim 1, wherein step (c) is performed through low gray-scale thresholding and spline interpolation.

16. The method of claim 1, wherein, for each pixel in the image acquired in step (a), step (b) comprises:
   (i) connecting a straight line from the pixel to a point in the image;
   (ii) computing an angle $\alpha$ of the straight line and a distance d from the pixel to the point;
   (iii) setting a window size s for local mean filtering according to s=kd, where k>0;
   (iv) locating a mean filtering window on the image, the mean filtering window centered on the pixel and perpendicular to the straight line; and
   (v) performing the mean filtering within the mean filtering window.

17. The method of claim 12, wherein step (b) further comprises automatic attenuation compensation.

18. The method of claim 6, wherein the point in the image is a predetermined point.

19. The method of claim 18, wherein the predetermined point in the image is at a bottom center of the image.

20. The method of claim 16, wherein the object comprises at least one organ of a living being.

21. The method of claim 20, wherein the living being is a human being, and wherein the at least one organ comprises a prostate ora urethra of the human being.

22. The method of claim 21, wherein step (a) comprises using ultrasound.

23. The method of claim 22, further comprising (e) segmenting a possible location of the urethra near a center of the prostate.

24. The method of claim 23, further comprising (f) forming a model of the prostate from the shape of the boundaries determined in step (d).

25. The method of claim 24, wherein the model formed in step (f) is a two-dimensional model.

26. The method of claim 24, wherein the model formed in step (f) is a three-dimensional model.

27. The method of claim 26, wherein each of steps (a)–(e) is performed a plurality of times to take a plurality of slices of the prostate to form the three-dimensional model.

28. The method of claim 16, wherein each of steps (a)–(d) is performed a plurality of times to take a plurality of slices of the object.

29. The method of claim 16, wherein step (c) is performed through low gray-scale thresholding and spline interpolation.

30. A method for mean filtering of an image, the method comprising, for every pixel in the image:
   (a) connecting a straight line from the pixel to a point in the image;

(b) computing an angle α of the straight line and a distance d from the pixel to the point;

(c) setting a window size s for local mean filtering according to s=kd, where k>0;

(d) locating a mean filtering window on the image, the mean filtering window centered on the pixel and perpendicular to the straight line; and (e) performing the mean filtering within the mean filtering window.

31. The method of claim 30, wherein the point in the pre-processed image is a predetermined point.

32. The method of claim 31, wherein the predetermined point in the pre-processed image is at a bottom center of the image.

33. A system for determining boundaries of an object, the system comprising:

(a) an imaging device for acquiring an image of a transverse cross-sectional outline of the object; and (b) a computing device, receiving the image from the imaging device, for pre-processing the image to remove noise and increase contrast so as to produced a pre-processed image, finding an edge of the object from a point in the pre-processed image, and locating key points of the boundaries of the object and connecting the key points under iterative training of a knowledge-based model until a shape of the boundaries of the object reaches a stable state.

34. The system of claim 33, wherein the imaging device comprises an ultrasound probe.

35. The system of claim 34, wherein the object comprises a human prostate, and wherein the computing device segments a possible location of a urethra near a center of the prostate.

36. The system of claim 35, wherein the computing device forms a model of the prostate from the shape of the boundaries.

37. The system of claim 36, wherein the model is a two-dimensional model.

38. The system of claim 36, wherein the model is a three-dimensional model.

39. The system of claim 38, wherein the ultrasound probe takes a plurality of slices of the prostate, and wherein the computing device uses the plurality of slices to form the three-dimensional model.

40. The system of claim 33, wherein the point in the pre-processed image is a predetermined point.

41. The system of claim 40, wherein the predetermined point in the pre-processed image is at a bottom center of the image.

42. The method of claim 35, wherein the computing device segments a possible location of an edge of a rectum near the prostate.

43. The system of claim 33, wherein the imaging device takes a plurality of slices of the object.

44. The system of claim 33, wherein the computing device finds the edge through low gray-scale thresholding and spline interpolation.

45. The system of claim 33, wherein, for each pixel in the image, the computing device pre-processes the image by:

(i) connecting a straight line from the pixel to a point in the image;

(ii) computing an angle α of the straight line and a distance d from the pixel to the point;

(iii) setting a window size s for local mean filtering according to s=kd, where k>0;

(iv) locating a mean filtering window on the image, the mean filtering window centered on the pixel and perpendicular to the straight line; and (v) performing the mean filtering within the mean filtering window.

46. The system of claim 45, wherein the computing device further pre-processes the image through automatic attenuation compensation.

47. The system of claim 45, wherein the point in the pre-processed image is a predetermined point.

48. The system of claim 47, wherein the predetermined point in the pre-processed image is at a bottom center of the image.

* * * * *

UNITED STATES PATENT AND TRADEMARK OFFICE
CERTIFICATE OF CORRECTION

PATENT NO.   : 6,561,980 B1
DATED        : May 13, 2003
INVENTOR(S)  : Gang Cheng, Haisong Liu and Yan Yu It is certified that error appears in the above-identified patent and that said Letters Patent is hereby corrected as shown below:

<u>Title page,</u>
Item [75], change last name of "Gheng" to -- Cheng --.

Signed and Sealed this

Eighth Day of July, 2003

JAMES E. ROGAN
*Director of the United States Patent and Trademark Office*